United States Patent [19]
Rosenthal

[11] Patent Number: 5,218,207
[45] Date of Patent: Jun. 8, 1993

[54] USING LED HARMONIC WAVELENGTHS FOR NEAR-INFRARED QUANTITATIVE

[75] Inventor: Robert D. Rosenthal, Gaithersburg, Md.

[73] Assignee: Futrex, Inc., Gaithersburg, Md.

[21] Appl. No.: 795,997

[22] Filed: Nov. 22, 1991

Related U.S. Application Data

[63] Continuation-in-part of Ser. No. 544,580, Jun. 27, 1990, Pat. No. 5,086,229, which is a continuation-in-part of Ser. No. 298,904, Jan. 19, 1989, Pat. No. 5,028,787.

[51] Int. Cl.$^5$ ............................................ G01N 33/50
[52] U.S. Cl. ................... 250/341; 250/339; 250/343; 128/633; 356/39
[58] Field of Search ............... 250/341, 339, 343; 128/633; 356/39

[56] References Cited

U.S. PATENT DOCUMENTS

| | | |
|---|---|---|
| 3,493,774 | 2/1970 | Knudsen . |
| 3,958,560 | 5/1976 | March ................................. 356/39 |
| 4,655,225 | 4/1987 | Dähne et al. ..................... 250/339 |
| 4,882,492 | 11/1989 | Schlager ............................ 250/341 |
| 4,883,953 | 11/1989 | Koashi et al. ..................... 250/341 |
| 4,975,581 | 12/1940 | Robinson et al. ................. 250/339 |
| 5,028,787 | 7/1991 | Rosenthal et al. ................ 250/341 |
| 5,086,229 | 2/1992 | Rosenthal et al. ................ 250/339 |

FOREIGN PATENT DOCUMENTS

| | | |
|---|---|---|
| 074428 | 3/1983 | European Pat. Off. . |
| 3619442 | 10/1986 | Fed. Rep. of Germany ...... 128/633 |
| 572309 | 2/1976 | Switzerland . |

OTHER PUBLICATIONS

Mueller et al., "Glucose Determination—State of the Art and Prospects," Biomedizinische Technik 25, 26–32 (1980); German language and translation.

*Primary Examiner*—Carolyn E. Fields
*Assistant Examiner*—Drew A. Dunn
*Attorney, Agent, or Firm*—Rothwell, Figg, Ernst & Kurz

[57] ABSTRACT

A near-infrared quantitative analysis instrument for measuring a constituent of a sample material is disclosed which effectively utilizes energy in the 1200 to 1800 nanometer wavelengths regions by isolating and employing harmonic wavelengths emitted by typical, low cost commercially available light emitting diodes (LEDs) or infrared emitting diodes (IREDs). The analysis instrument utilizes these very desirable wavelength regions for quantitative analysis measurements by interposing suitable narrow bandpass filters which permit passage of only the selected harmonic wavelengths.

14 Claims, 6 Drawing Sheets

USING LED HARMONIC WAVELENGTHS FOR NEAR-INFRARED QUANTITATIVE

This application is a continuation-in-part of copending application Ser. No. 544,580, filed Jun. 27, 1990, now U.S. Pat. No. 5,086,229, which is a continuation-in-part of Ser. No. 298,904, filed Jan. 19, 1989, now U.S. Pat. No. 5,028,787.

BACKGROUND OF THE INVENTION

1. Field of the Invention

This invention relates to instruments and methods for the non-invasive quantitative measurement of constituents in material samples, such as protein in wheat and glucose levels in a test subject's blood. Specifically, this invention relates to a novel near-infrared quantitative measurement instrument which utilizes harmonic wavelengths of light emitting diodes (LEDs).

2. Description of the Background Art

The use of LEDs and IREDs as energy sources for near-infrared measurements is a well established art. For example, thousands of TREBOR-90/XL Wheat and Barley Testers, which use IREDs as energy sources, are currently being used in country elevators for measuring the protein and moisture content in wheat and barley. Similarly, over 10,000 FUTREX-5000 Body Composition Analyzer Instruments, which also utilize IREDs, are currently being used in medical institutions, health clubs and sporting teams for measuring percent body fat. Also, a combination of LEDs and IREDs are currently being used in non-invasive near-infrared quantitative analysis instruments to assess the chemical composition of the blood, such as measurement of blood glucose levels.

One common limitation of the current generation of instruments which use LEDs/IREDs is that they are generally limited to wavelengths below approximately 1100 nanometers. This limitation is primarily due to the fact that the longest wavelengths emitted by commercially available, low cost LEDs/IREDs is typically approximately 950 nanometers. Even with the use of narrow bandpass filters located outside the IRED's half power bandwidth (see U.S. Pat. No. 4,286,327, incorporated herein by reference), typical IREDs do not provide a practical means of making measurements above approximately 1050 nanometers.

Although there are commercially available IREDs having wavelengths between 1000 and 1700 nanometers, such energy sources are extremely expensive and have a very low power output. For example, Model IR-1300 (UDT Sensors, Inc.) is an IRED that emits 20 microwatts of optical energy at 1300 nm and costs more than $30. In comparison, a typical LED emits approximately 1000 times more energy and costs less than $0.30.

As illustrated in FIG. 1, the spectrum ranges in the vicinity of 1200 to 1800 nanometers can be very important in performing quantitative measurements. This results from the fact that some absorption peaks for fat, starch and protein do not overlap the dominant water absorptions in this region. For example, at 1200 nm there is a relatively strong fat absorption band with almost no interfering absorption occurring from water. In most other regions of the spectrum, the infrared energy absorption by water significantly overlaps with the infrared energy absorption by other organic constituents such as oil, starch and protein. Thus, accurately performing quantitative measurements of such organic constituents in these lower wavelengths can be hindered by interference with water absorption.

FIG. 2 illustrates the fact that, in lower wavelength regions, infrared energy absorption by water significantly overlaps with the absorption by other organic constituents. In contrast, water absorption at 1200 and between 1600 and 1800 nanometers do not significantly interfere which makes the measurements of protein, oil/fat, starch and other constituents considerably attractive in these regions.

For example, U.S. Pat. No. 5,028,787, incorporated herein by reference, teaches a method of performing near-infrared noninvasive measurement of blood glucose levels using energy in the 600 to 1100 nanometer spectrum region. Constituent absorptions in this region are weaker than in the 1200 nanometer region. As a consequence, measurement of organic constituents in products containing water often result in major mutual interference from water. Thus, although glucose measurements in the 600 to 1100 nanometer region of the spectrum are practical, such measurements are necessarily more complex than potential measurement at 1200 or 1600–1800 nanometers.

Thus, there is a great need for a near-infrared quantitative measurement instrument having a solid state energy source (IRED) which can provide reasonable energy in the 1200 to 1800 nanometer region and yet which is reasonably priced.

SUMMARY OF THE INVENTION

In accordance with the present invention, a near-infrared quantitative analysis instrument for measuring a constituent of a sample material comprises an introducing means including a near-infrared energy source for introducing near-infrared energy into a sample material wherein the energy source emits radiation at a peak wavelength and at harmonic wavelengths. The instrument further comprises a filter means for filtering the near-infrared energy at all wavelengths except in regions of a selected one of the harmonic wavelengths. The instrument utilizes a detecting means for detecting the energy emerging from the sample and a processing means for processing an electric signal produced by the detecting means into a signal indicative of the constituent present in the sample.

In accordance with another aspect of the present invention, a near-infrared quantitative analysis instrument for measuring blood glucose comprises an introducing means for introducing near-infrared energy into blood present in a body part of a subject. The instrument further comprises a filter means for selectively filtering the near-infrared energy at all wavelengths except in a region of one of the harmonic wavelengths of the introducing means. The Instrument utilizes a detecting means for detecting near-infrared energy emerging from the subject and means for converting an electrical signal corresponding to the detected energy into a signal indicative of the quantity of glucose present in the blood of the subject.

DETAILED DESCRIPTION OF THE PREFERRED EMBODIMENTS

Figure 1:
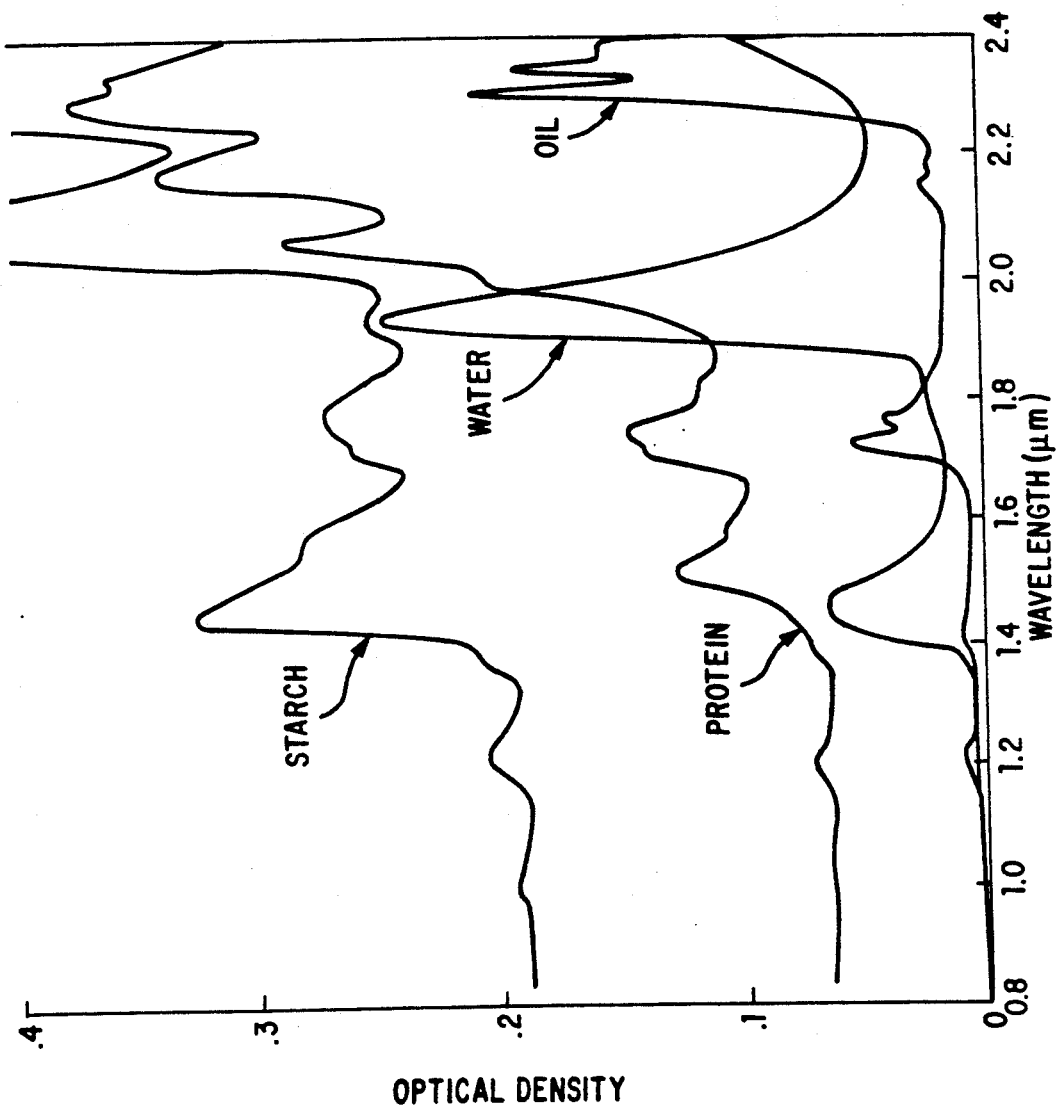
FIG. 1 is a plot of Log (1/I) versus wavelength illustrating near-infrared energy absorption spectra for water, starch, oil and protein in the 1200 and 1600 nanometer regions.
Figure 2:
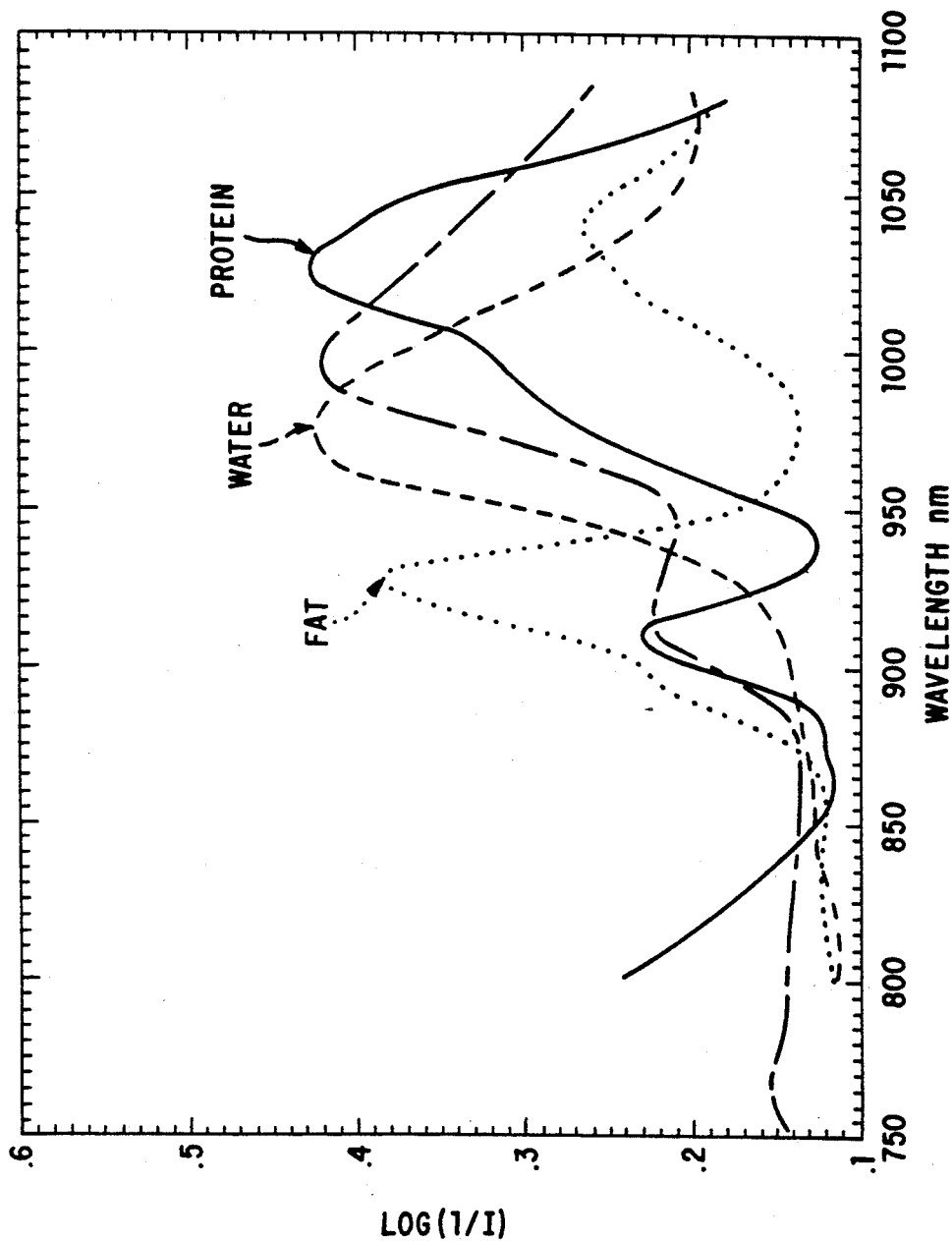
FIG. 2 is a plot of Log (1/I) versus wavelength illustrating that the near-infrared energy absorption peaks of water overlap with the absorption peaks of fat and protein in the 900 to 1050 nanometer region.
Figure 3:
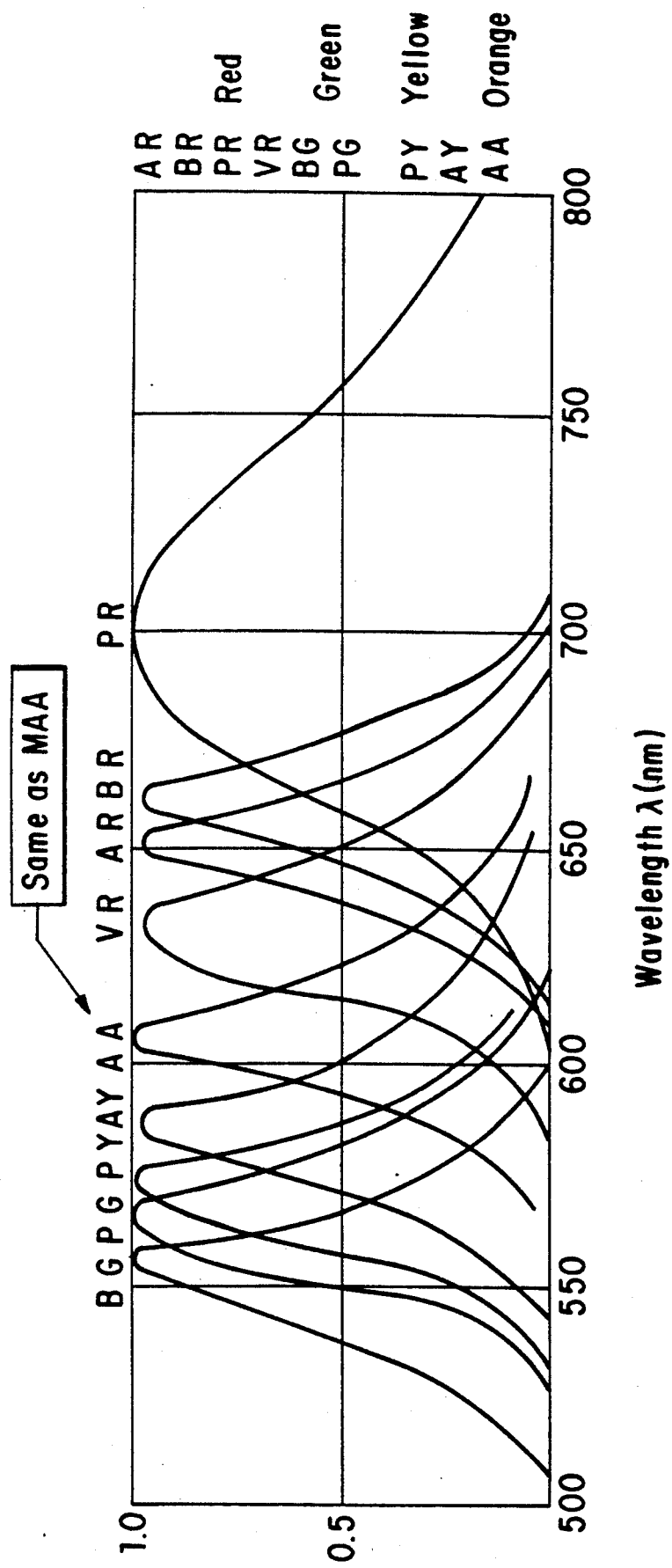
FIG. 3 illustrates the energy spectrum of a known IRED.

The near-infrared quantitative measurement instrument according to the present invention effectively utilizes energy in the 1200 to 1800 nanometer regions by isolating and employing harmonic wavelengths emitted by typical, low cost commercially available LEDs. A typical LED is designed to emit energy at a center wavelength which has a reasonably narrow half-power bandwidth. For example, FIG. 3 shows the spectrum of a typical LED, from Stanley Electronics Company Ltd. (Tokyo, Japan), which has a center wavelength at approximately 600 nanometers with a half power bandwidth of 35 nanometers (Stanley Part Number MAA33685). Such LEDs are used in many commercial products and are very low priced, e.g. typical price is less than $0.30 each.

Figure 4:
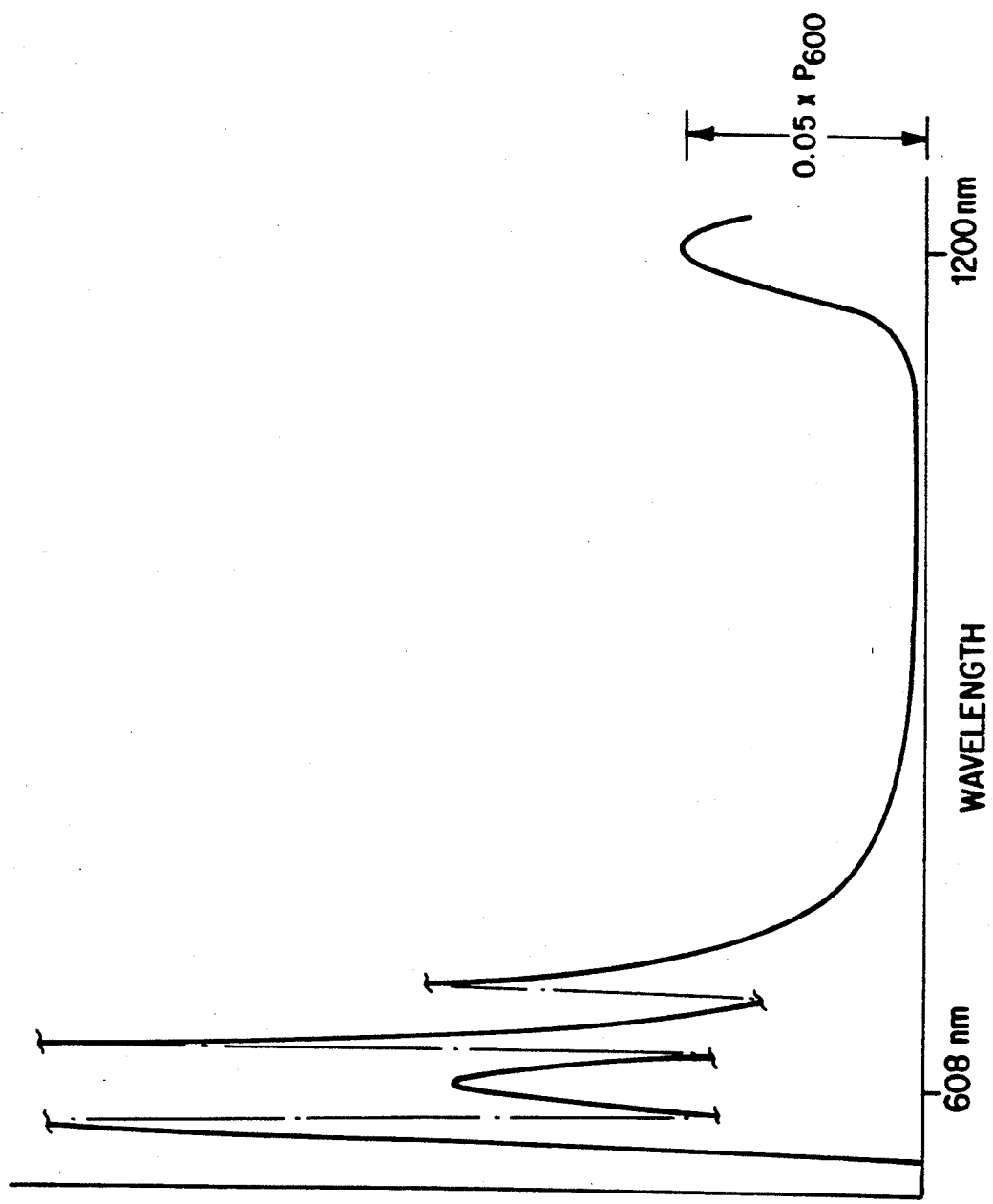
FIG. 4 illustrates the center wavelength and a harmonic wavelength of a known IRED.

These typical LEDs also have been discovered to emit light at a harmonic wavelength in the near-infrared region. For example, FIG. 4 shows the spectra of an "MAA" type LED, the same LED described in FIG. 3, measured with a precision spectrophotometer, i.e. a Cary-14 Spectrophotometer. FIG. 4 illustrates that MAA the center wavelength of "MAA" type LED is approximately 608 nanometers which is reasonably identical to the 604 nanometer center shown in FIG. 3. FIG. 4 also illustrates that there is energy emitted form this low cost part which peaks at approximately 1200 nanometers with a half power bandwidth of approximately 180 nanometers. These figures show that the standard Stanley "MAA" type LED provides optical energy not only in the normal visible band of approximately 604 nanometers, but also in the near-infrared 1200 nanometer region.

The amount of energy at the 1200 nanometer region is approximately 5% of the peak energy at the 604 nanometer region. Although this number may not appear to be large, it is more than that generated by the custom made IRED for 1200 nanometers. Moreover, because of the wide half-power bandwidth at 1200 nanometers, i.e. 180 nanometers, it means that many measurement wavelengths can be generated through use of either multiple MAA type LED's, each with its own narrow band pass optical filter, or through use of a "filter wheel" which contains a number of optical filters and which is positioned in the light beam of the LED.

The spectrum of each "IRED" is limited by the use of suitable narrow bandpass optical filters both within a half power bandwidth and outside the half power bandwidth, as taught in U.S. Pat. No. 4,286,327, incorporated herein by reference.

Figure 5:
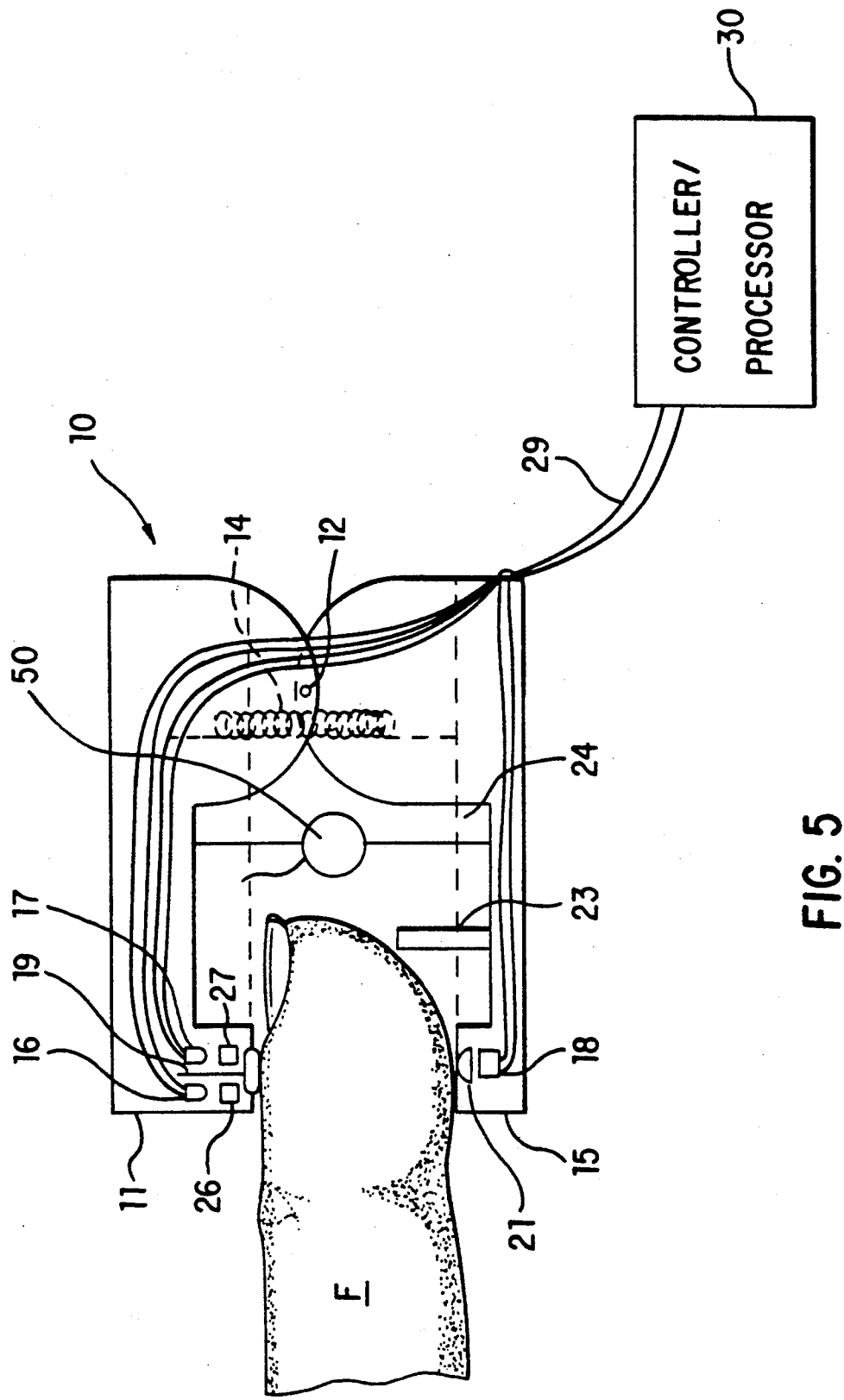
FIG. 5 is a near-infrared quantitative analysis instrument according to the present invention.

A near-infrared quantitative analysis instrument according to the present invention will be described with reference to FIG. 5 which shows a lightweight handheld analysis instrument 10 which measures a blood analyte present in a body part, e.g. blood glucose levels.

The analysis instrument 10 includes an introducing means for introducing near-infrared energy into blood present in a body part of a test subject. The introducing means comprises at least one standard, low cost LED, such as the Stanley MAA type LED discussed above, which emits energy at a central wavelength and at harmonic wavelengths. Two such LEDs 16 and 17 are illustrated in FIG. 5 and are positioned within an upper flange 11. Each LED is optically isolated via opaque light baffle 19.

The upper flange 11 is hinged about shaft 12 to lower flange 15, and a spring 14 serves to maintain the flanges in a closed position. An optical detector 18 is disposed in lower flange 15 opposite the LEDs 16 and 17. The detector is disposed behind an optional window 21 which can be constructed of a material which is either optically clear or which excludes visible light yet permits near-infrared light to pass. A finger stop 23 helps place and maintain the subject's finger in its proper position within the instrument 10. Each of the flanges is provided with light-shielding barriers 24 (shown in phantom in FIG. 5) to block ambient light from entering the instrument.

A filtration means is positioned between the LEDs and a test subject's body part for selectively filtering the energy emitted by the introducing means and for passing only energy in the region of a selected harmonic wavelength of the LEDs. The filtration means can be any filter or system of filters which pass only energy in a selected wavelength region. For example, filters 26 and 27, illustrated in FIG. 5, are narrow band pass filters which pass energy emitted by LEDs 16 and 17 only in the region of the harmonic wavelength, i.e. approximately 1200 nanometers. Any suitable narrow bandpass filters may be used.

Operation of the near-infrared quantitative analysis instrument 10 according to the present invention will be discussed as follows. The finger of a test subject is inserted between flanges 11 and 15 of the instrument 10. Light energy emitted from LEDs 16 and 17 is filtered by narrow bandpass filters 26 and 27 and is transmitted through the test subject's finger and is detected by optical detector 18. Detector 18 can be any suitable detector for detecting energy in near-infrared wavelength region, such as a lead sulfide (PbS) detector. An indium arsenide (InAs) detector can be used as well.

The electric signals produced by the detectors are transmitted via line 29 to a controller processor unit 28 where the signal is amplified and data processed using a suitable algorithm, such as those disclosed in U.S. Pat. No. 5,028,787 ("the '787 patent"), and displayed on a readout device. However, because there is less interference in these wavelength regions, an algorithm, such as those described in the '787 patent, can be used which has fewer regression terms. Using an algorithm having fewer regression terms makes the apparatus more simple and inexpensive. Also, potentiometer 50 is utilized to permit measurement of a patient's finger thickness.

Figure 6:
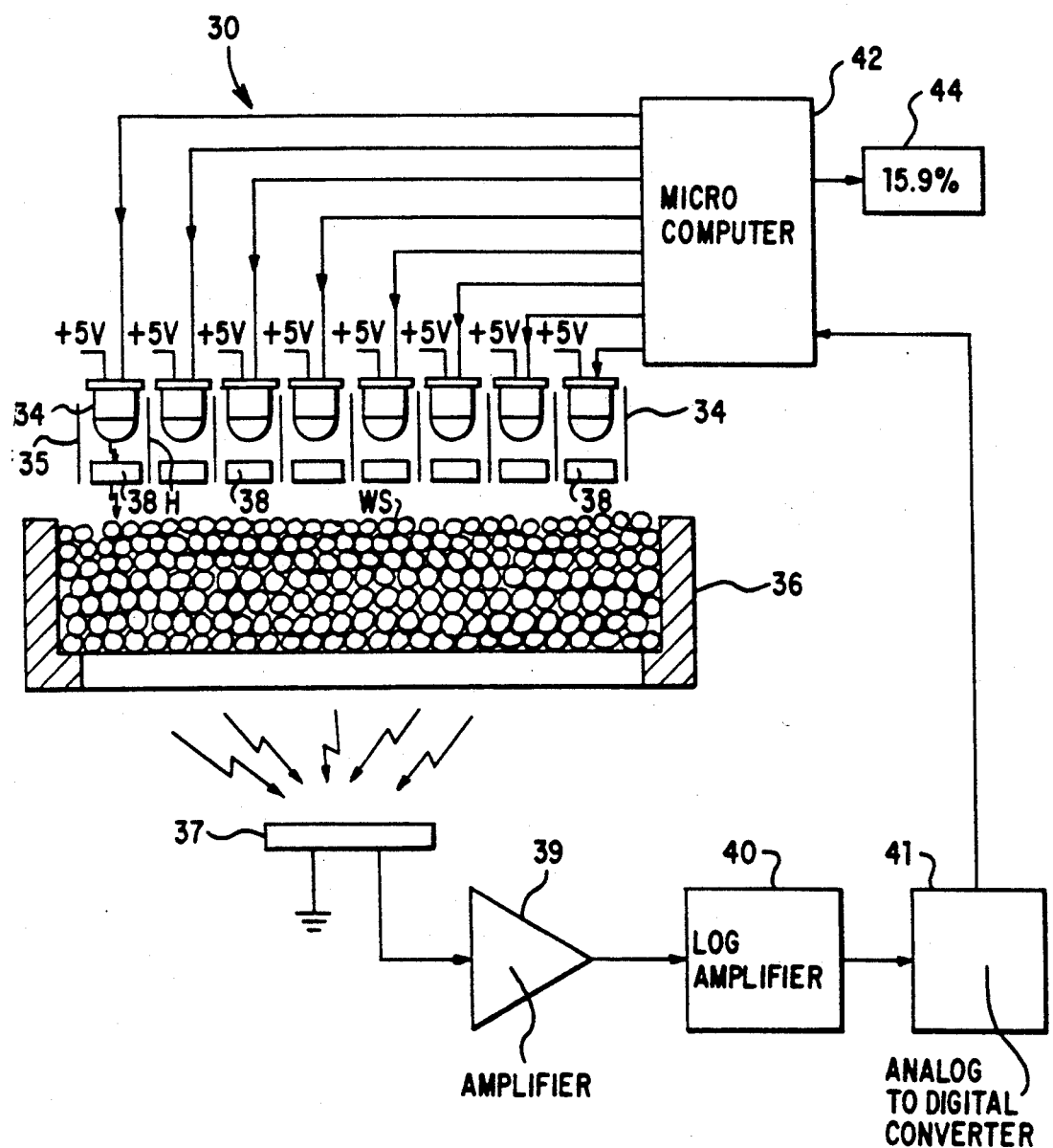
FIG. 6 is a near-infrared quantitative analysis instrument according to an second embodiment of the present invention.

A near-infrared quantitative analysis instrument according to another embodiment of the present invention will be described with reference to FIG. 6 which shows a near-infrared analysis instrument 30 for measuring the a constituent present in a sample material, such as protein in wheat. Analysis instrument 30 includes an introducing means for introducing near-infrared energy into a material sample. In the FIG. 6 embodiment, a wheat sample is shown supported by container means 36. The introducing means comprises at least one standard, low cost LED, such as the Stanley MAA type LED discussed above, which emits energy at a central wavelength and at harmonic wavelengths. For example, LEDs 34 are illustrated in FIG. 6 which are optically isolated via opaque light baffles 35. In the specific embodiment shown in FIG. 6, the microprocessor 42 is programmed to allow only one of the LEDs to be turned on at a time and automatically sequences all LEDs, as disclosed in U.S. Pat. No. 4,286,327.

The filtration means is positioned between the LEDs and the sample material for selectively filtering the energy emitted by the introducing means and for passing energy only in the region of a selected harmonic wavelength of the LEDs. For example, narrow band pass filters 38 pass energy emitted by the LEDs 34 only in the region of the harmonic wavelength, i.e. approximately 1200 nanometers. Any suitable means for blocking all wavelengths but only a desired wavelength region may be used. Further, the filter means can permit the passage of energy from any selected harmonic wavelength emitted by the LEDs.

The energy transmitted through the sample material is detected by detecting means 37 which can be any suitable detector such as those described above in connection with FIG. 5. Electric signals produced by the detecting means are amplified via amplifier 39 and log amplifier 40 and are digitized in analog to digital converter 41. The digitized signals are transmitted to microprocessor 42 and data processed using any suitable algorithm, such as those described in the '787 patent. The sample material's constituent concentration is displayed on readout device 44.

Although the invention has been described in connection with certain preferred embodiments, it is not limited to them. Modifications within the scope of the following claims will be apparent to those skilled in the art. For example, accurate measurements can be obtained from body parts other than the finger, e.g. the wrist. The algorithm used to calculate the sample constituent concentration(s) can be altered in accordance with known near-infrared analytical techniques.

I claim:

1. A near-infrared quantitative analysis instrument for non-invasive measurement of a constituent present in a sample material, comprising:
   (a) introducing means including a near-infrared energy source for introducing near-infrared energy into said sample material, said near-infrared energy source emitting near-infrared energy at a peak wavelength and at harmonic wavelengths;
   (b) filter means for filtering said near-infrared energy at said peak wavelength and for passing energy only at a selected one of said harmonic wavelengths;
   (c) detecting means for detecting near-infrared energy emerging from the sample material;
   (d) processing means for processing an electric signal produced by said detecting means into a signal indicative of the quantity of said constituent present in said sample.

2. The near-infrared quantitative analysis instrument set forth in claim 1 wherein said near-infrared energy source is an light emitting diode (LED), or an infrared emitting diode (IRED).

3. The near-infrared quantitative analysis instrument set forth in claim 1 wherein said peak wavelength of said near-infrared energy source is at approximately 604 nanometers.

4. The near-infrared quantitative analysis instrument set forth in claim 3 wherein said near-infrared energy source is a near-infrared energy source having a harmonic wavelength at approximately 1200 nanometers.

5. The near-infrared quantitative analysis instrument set forth in claim 1 wherein said filter means permits the passage of energy only at approximately 1200 nanometers.

6. A near-infrared quantitative analysis instrument for non-invasive measurement of a blood analyte present in a body part of a subject, comprising:
   (a) introducing means including a near-infrared energy source for introducing near-infrared energy into said body part of said subject, said near-infrared energy source emitting near-infrared energy at a peak wavelength and at harmonic wavelengths;
   (b) filter means for filtering said near-infrared energy at said peak wavelength and for passing energy only at a selected one of said harmonic wavelengths;
   (c) detecting means for detecting near-infrared energy emerging from said body part of said subject;
   (d) processing means for processing an electric signal produced by said detecting means into a signal indicative of the quantity of said blood analyte present in said body part of said subject.

7. The near-infrared quantitative analysis instrument set forth in claim 6 wherein said blood analyte is a blood glucose level present in the blood in said body part.

8. The near-infrared quantitative analysis instrument set forth in claim 6 wherein said near-infrared energy source is a light emitting diode (LED) or IRED.

9. The near-infrared quantitative analysis instrument set forth in claim 6 wherein said peak wavelength of said near-infrared energy source is at approximately 604 nanometers.

10. The near-infrared quantitative analysis instrument set forth in claim 9 wherein said near-infrared energy source is a near-infrared energy source having a harmonic wavelength at approximately 1200 nanometers.

11. The near-infrared quantitative analysis instrument set forth in claim 6 wherein said filter means permits the passage of energy only at approximately 1200 nanometers.

12. A non-invasive method for quantitatively analyzing a constituent present in a sample material, comprising:
   (a) introducing near-infrared energy from a near infrared energy source into said sample material, said near-infrared energy source emitting near-infrared energy at a peak wavelength and at harmonic wavelengths;
   (b) filtering said near-infrared energy at said peak wavelength and passing energy only at a selected one of said harmonic wavelengths;
   (c) detecting near-infrared energy emerging from the sample material; and
   (d) processing an electric signal produced by said detecting means into a signal indicative of the quantity of said constituent present in said sample.

13. The non-invasive method as set forth in claim 12 wherein said peak wavelength of said near-infrared energy source is at approximately 604 nanometers.

14. The non-invasive method as set forth in claim 13 wherein said near-infrared energy source is a near-infrared energy source having a harmonic wavelength at approximately 1200 nanometers.

* * * * *